(12) United States Patent
Thiebaud et al.

(10) Patent No.: US 7,887,509 B2
(45) Date of Patent: Feb. 15, 2011

(54) FLUID VOLUME MEASUREMENT DEVICE FOR MEDICAL USE

(75) Inventors: Pierre Thiebaud, Cressier (CH); Didier Vecten, Ballens (CH); Yvan Favre, Prilly (CH); Hans-Gerd Evering, Corseaux (CH)

(73) Assignee: Debiotech S.A., Lausanne (CH)

( * ) Notice: Subject to any disclaimer, the term of this patent is extended or adjusted under 35 U.S.C. 154(b) by 123 days.

(21) Appl. No.: 12/158,500

(22) PCT Filed: Dec. 29, 2006

(86) PCT No.: PCT/IB2006/055055

§ 371 (c)(1),
(2), (4) Date: Nov. 10, 2008

(87) PCT Pub. No.: WO2007/074425

PCT Pub. Date: Jul. 5, 2007

(65) Prior Publication Data

US 2009/0149811 A1 Jun. 11, 2009

(30) Foreign Application Priority Data

Jan. 25, 2006 (EP) .................................. 06100822

(51) Int. Cl.
*A61F 7/12* (2006.01)
*A61F 7/00* (2006.01)
(52) U.S. Cl. ........................ 604/114; 604/113; 392/470
(58) Field of Classification Search ....................... None
See application file for complete search history.

(56) References Cited

U.S. PATENT DOCUMENTS

| 4,384,578 A | * | 5/1983 | Winkler ........................ 604/114 |
| 6,257,265 B1 | * | 7/2001 | Brunner et al. ................. 137/1 |
| 2003/0135250 A1 | * | 7/2003 | Lauman et al. ............. 607/104 |

FOREIGN PATENT DOCUMENTS

| WO | 92/17040 | 10/1992 |
| WO | 02/36187 | 5/2002 |
| WO | WO 0236187 A2 * | 5/2002 |

OTHER PUBLICATIONS

International Search for PCT/IB2006/055055 mailed May 30, 2007.
Written Opinion for PCT/IB2006/055055 mailed May 30, 2007.

* cited by examiner

*Primary Examiner*—Nicholas D Lucchesi
*Assistant Examiner*—Ian K Holloway
(74) *Attorney, Agent, or Firm*—Nixon & Vanderhye P.C.

(57) ABSTRACT

Medical device for the delivery and/or the extraction of fluid to and/or from a patient, said medical device comprising a pumping unit (1) for pumping a fluid, a warming chamber (2) with an inlet (3) and an outlet (4) and containing a heating element (5) for warming said fluid, fluid volume measuring means (13-18) and a fluid line crossing said pumping and warming units (1, 2), characterized by the fact that said heating element (5) is adapted to be fully immersed in the fluid which is crossing said warming chamber (2) and by the fact that said fluid measuring means comprise temperature sensing means adapted to measure the fluid temperature on at least two separate points and electrical parameter measuring means for determining at least one electrical parameter such as current, power or frequency applied to said heating element (5). The invention also includes a method for using this device.

25 Claims, 5 Drawing Sheets

FLUID VOLUME MEASUREMENT DEVICE FOR MEDICAL USE

Figure 1:
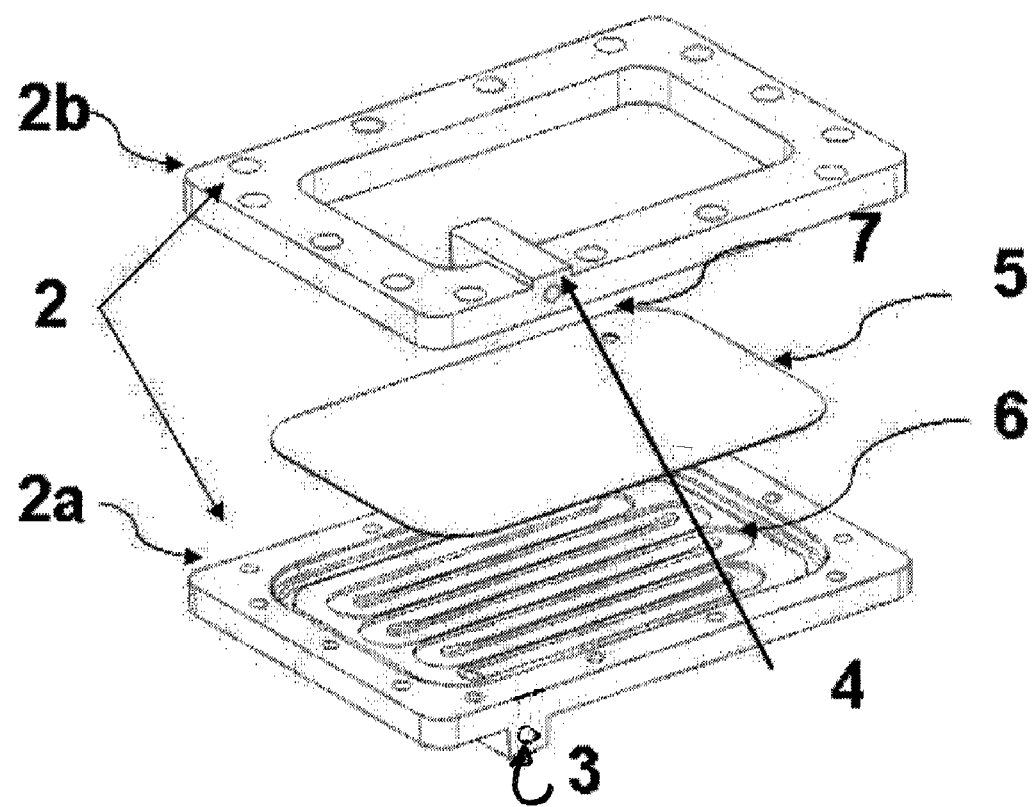

This application is the U.S. national phase of International Application No. PCT/IB2006/055055 filed 29 Dec. 2006 which designated the U.S. and claims priority to International Application No. PCT/IB2005/054426 filed 29 Dec. 2005 and European Patent Application No. 06100822.3 filed 25 Jan. 2006, the entire contents of each of which are hereby incorporated by reference.

FIELD OF INVENTION

The present invention relates to the volume measurement of fluids in the medical field. The invention preferably concerns medical liquids such as saline solutions, dialysis liquids or dialysis substitution liquids.

STATE OF THE ART

A wide range of different fluid therapy treatments require the infusion of medical solutions, like saline solutions, dialysis fluids or dialysis substitution fluids.

In all cases, a pumping system is used to handle these fluids in high volumes. For these fluid therapies, two requirements are essential for the patients benefit.

Firstly, the fluids must be warmed up to the comfortable fluid temperature for the patient, which should be safe and adjustable to the body temperature. Secondly, for certain treatments, like Peritoneal Dialysis (PD) and Haemodialysis (HD), it is essential to measure the exact applied fluid volume to the patient. Furthermore, the extracted fluid volumes, like drain fluid during PD and Ultrafiltrate during HD requires exact fluid volume measurement and balancing.

Methods and devices for measuring fluid volumes are disclosed in patent documents U.S. Pat. No. 4,384,578, U.S. Pat. No. 5,245,693, U.S. Pat. No. 6,257,265, U.S. Pat. No. 6,512,212 and US 2003/135250.

GENERAL DESCRIPTION OF THE INVENTION

The present invention provides an improvement with respect to the state of the art.

To this effect, the object of the invention consists of a medical device for the delivery and/or the extraction of fluid to and/or from a patient, said medical device comprising a pumping unit for pumping a fluid, a warming chamber with an inlet and an outlet and containing a heating element for warming said fluid, fluid volume measuring means and a fluid line crossing said pumping and warming units. The device according to the invention is characterized by the fact that the heating element is adapted to be fully immersed in the fluid which is crossing said warming chamber and by the fact that said fluid volume measuring means comprise temperature sensing means adapted to measure the fluid temperature on at least two separate points, said fluid measuring means furthermore comprising electrical parameter measuring means for determining at least one electrical parameter such as current, power or frequency applied to the heating element.

In a first embodiment, the temperature sensing means consist of one single temperature sensor. Such a configuration provide a higher precision in the measurement. There is in particular no need to calibrate two separate temperature sensors.

The single sensor may is movably mounted in such a way as to measure the temperature on said two separate points.

Advantageously the single sensor rotatable.

In another embodiment the temperature sensing means comprise one fixed temperature sensor and one rotatable mirror which is adapted to reflect to said sensor the electromagnetic emission from said two separate points.

In this case the sensor is preferably of the infrared type.

The mirror taken, as such is not necessarily rotatable but may be mounted on a rotatable platform. MEMS technology can be used to manufacture the mirror, with or without a rotatable platform When using a single sensor, a preferred location is between the inlet and the outlet of the warming chamber. But of course, any other suitable location can be taken.

In another embodiment the temperature sensing means comprise two separate temperature sensors. As indicated above, the precision may be decreased but such a configuration may be easier to obtain.

When using two separate sensors, one sensor is preferably located close to the inlet while the other is located close to the outlet.

In another embodiment the medical device furthermore comprises a processing unit connected to said temperature sensor(s), the processing unit being adapted to measure the volume flow through the warming unit and the volume flow is derived from the fluid volume measuring means.

The temperature sensor(s) may be designed to permanently measure the temperature or to measure the temperature only during a predefined period during the warming phase.

In another embodiment the medical device comprises fluid volume compensating means which are connected to said processing unit and to said pumping unit.

The heating element is preferably made of metal and is designed to be heated by electromagnetic induction.

In one embodiment the heating element is a plate while in another embodiment it has a tubular shape.

In order to increase the length of the fluid line in the warming chamber, i.e. to increase the heat exchange, the fluid line may have a spiral or winded shape in the warming chamber, forming thereby a several parallel fluid channels.

In another embodiment the medical device comprises an inductive element consisting of at least one coil.

Preferably the coil is made of isolated strands having a diameter which is less than the penetration depth of the magnetic field in the heat conductive metallic element.

Advantageously the diameter is at least two times less than said penetration depth.

In another embodiment the heating element is designed and situated in a way as to act as an electromagnetic shielding element to prevent electromagnetic perturbations outside of the warming system.

The heating element may be made of a ferromagnetic material with a Curie temperature selected to limit overheating of the heat conductive metallic element.

The invention also relates to the use of a medical device as defined above for measuring the volume of the fluid crossing the device, the fluid volume being derived from the measurement of the temperature taken on at least two separate points of the fluid line and from the measurement of at least one electrical parameter such as current, power or frequency applied to the heating element.

Advantageously the device may also be used for compensating volume changes between a patient inflow and outflow.

In one embodiment a part of the volume pumped is warmed for the sole purpose of measuring its flow characteristics.

From the above description, it can be seen that the invention takes benefit from the warming system in order to measure fluid volumes and/or flow, and more precisely fluid volume changes.

The invention combines technical solutions for warming and balancing fluid volumes during fluid therapies, which are administered and extracted from patients by all kinds of pumping systems. More generally the invention can be used in conjunction with all forms of pumps to achieve accurate fluid volume balancing by fluid volume delivery compensation.

In order to measure and balance fluid volumes it may be advantageous to measure both the inflow and outflow for at least one part of the entire volume pumped. Also in case warming is not needed for the outflow (e.g. drain volume during PD), it may be required to warm part of such volume for the sole purpose of measuring the flow volume.

In particular, the present invention allows the use of a sterile disposable in combination, without any physical contact, between the medical fluid and the warming system and, if present, the measuring elements.

DETAILED DESCRIPTION OF THE INVENTION

The invention is discussed below in a more detailed way with examples illustrated by the following figures:

FIG. 1: Exploded view of a warming chamber according to the invention
FIG. 2: Bottom view of the warming chamber of FIG. 1
FIG. 3: Electrical induction circuit
FIG. 4: Fluid volume delivery compensation diagram
FIG. 5: Integrated Heating Chamber with Fluid Distribution System and Pump

NUMERICAL REFERENCES USED IN THE FIGURES

1. Pumping unit
2. Warming chamber
3. Inlet
4. Outlet
5. Heating element
6. Channel
7. Hole
8. Coil
9. Ferrite core
10. Cover plate
11. Fluid distribution unit
12. Electrical induction circuit
13. Temperature sensor
14. Current measuring means
15. Voltage measuring means
16. Power measuring means
17. Current frequency measuring means As it can be seen on FIG. 1, a medical fluid, which can be driven by a variety of pumps such as a peristaltic pump, flows into a rigid warming chamber 2, consisting of a lower part 2a and a upper part 2b which, e.g. may be made of plastic. The warming chamber 2 has an inlet port 3 and an outlet port 4 which are connected to a tubing (not illustrated). The chamber 2 contains an integrated metallic plate 5 which preferably consists out of ferromagnetic material. The flow channel geometry in the chamber parts 2a and 2b in combination with the metallic plate 5 ensure, that the fluid entering the chamber part 2a at the inlet port 3 flows directly into specific shaped channels 6 which are situated under a first side of the metallic plate 5. The channels 6 are then extending over the second side of the metallic plate 5 and the fluid is finally exiting the chamber 2b trough the outlet port 4.

The mechanical design of the heating chamber 2 ensures that the metallic plate 5 separates the chamber 2 in two parts. Preferably, with the exception of the channels 6 and a hole 7 in the metallic plate 5, there is no fluid exchange between the two parts. With such a configuration the fluid initially flows on one face and then on the other face of the metallic plate 5.

Figure 2:
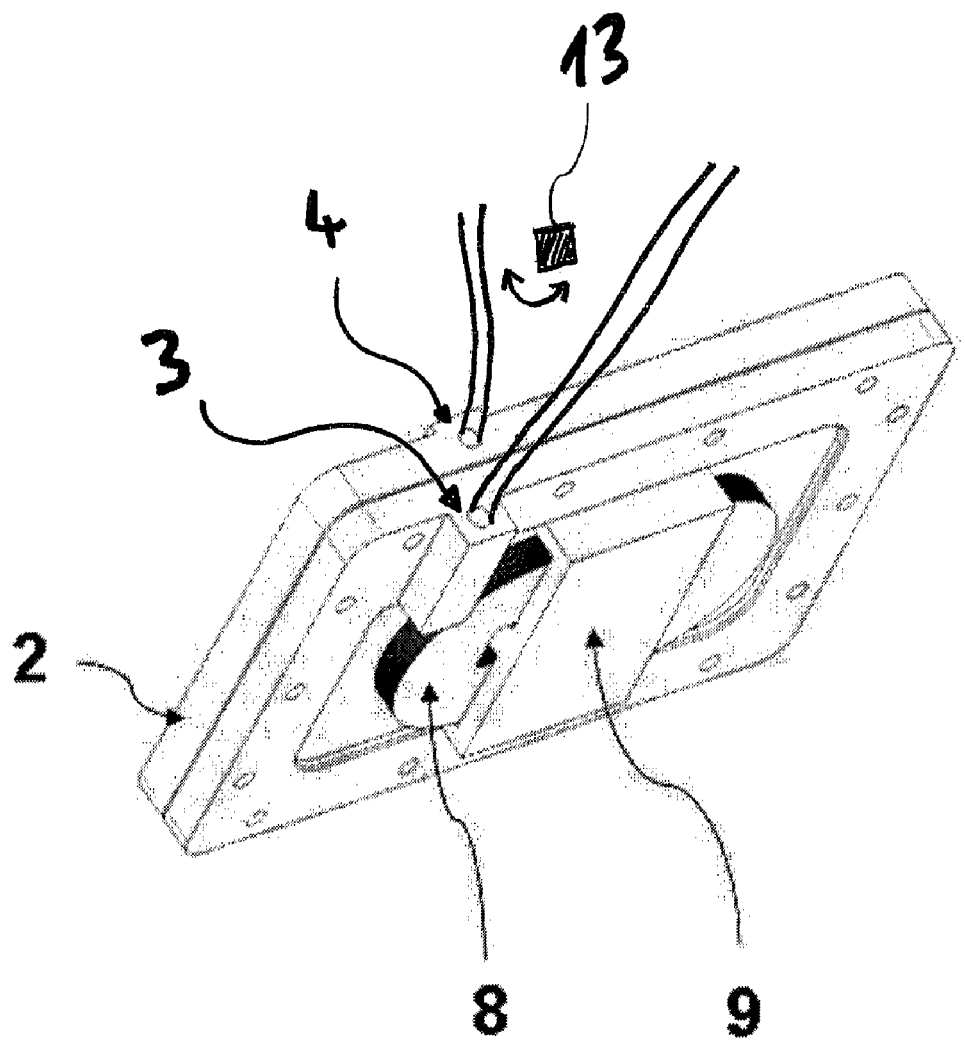

FIG. 2 shows a coil 8 for a induction heating. In combination with a specific ferrite core 9 the coil 8 is used to induct a electromagnetic field into the metallic plate 5 (not shown). For the delivery of e.g. 600 Watt electrical power at 110 Volt AC a current of 5.45 Ampere RMS is required. In order to minimize the electronic complexity and satisfy the requirements in accordance to various norms, frequencies from 50 kHz to 100 kHz can be used. To avoid any active cooling of the coil 8 (e.g. with water) a improved coupling between the metallic plate 5 and the coil 8 may be achieved by concentrating the magnetic flux moving through the metallic plate 5. A ferromagnetic metallic plate 5 may be used to concentrate the energy in a very thin layer. In combination with a ferrite core 9 around the coil 8 a significant improvement of the coupling factor may be achieved and may reduce the resistance of the magnetic flux path. A further improvement may be achieved for the coupling factor in specifying the distance between the coil 8 and the metallic plate 5.

To reduce the self induction of the coil 8 at the used frequencies, eddy current losses as well as proximity effect between layers, the coil design may consist of specific number of bunch of isolated copper strands with a diameter which shall be preferably two or three times less than the penetration depth.

Advantageously the heating unit is combined with one or more temperature sensors, e.g. contact less infrared temperature sensors. The temperature sensors are adapted and/or separated for measuring the temperature of the fluid which enters and/or exits the chamber 2. The temperature data are used to calculate the internal energy change of the fluid which crosses the chamber 2.

On FIG. 2, a single temperature sensor 13 is schematically illustrated. It is located between the inlet and the outlet line and can rotate in order to alternatively measure the temperature on the inlet or on the outlet line.

In another embodiment (not illustrated) a fixed sensor with a rotatable mirror is used. In this case, the sensor is preferably of the infrared type.

Figure 3:
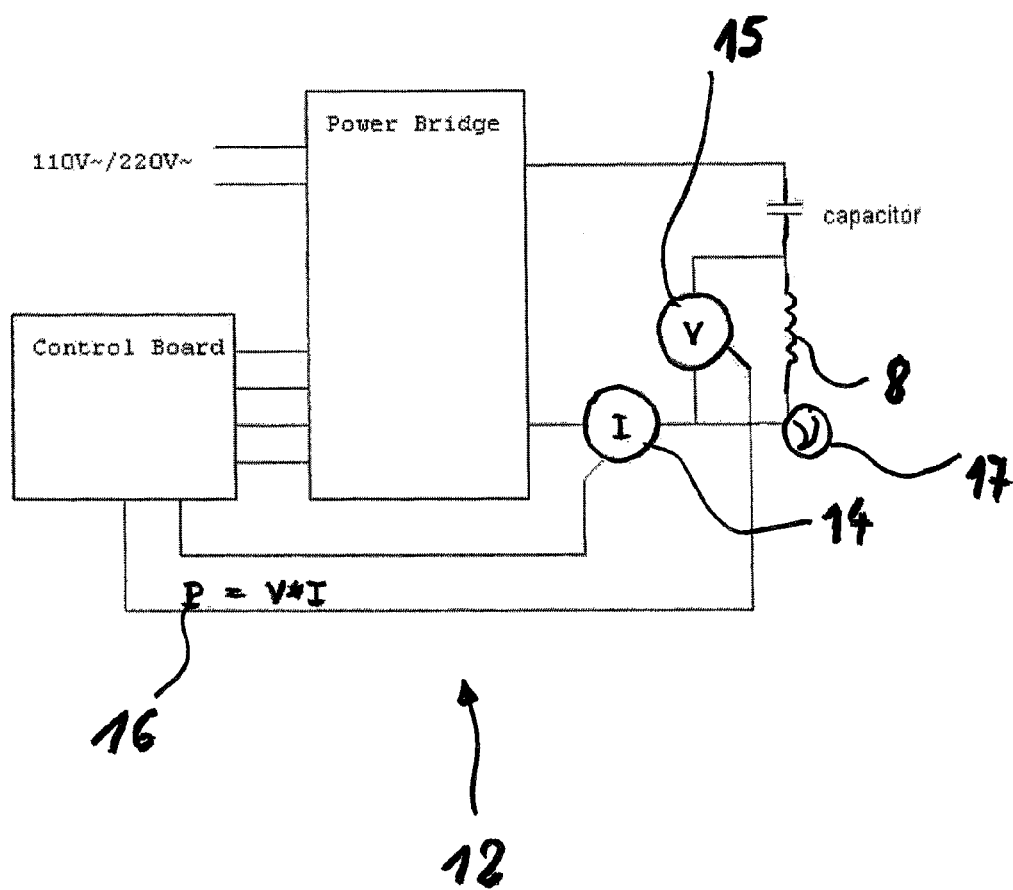

FIG. 3 shows an electrical induction circuit 12 which may be used in the medical device according to the invention. This configuration allows to determine the fluid energy change from the measurement of the electrical power 14,15,16 and/or the current 14 and/or the frequency 17 applied to the coil 8 to obtain or maintain a certain temperature of the fluid near e.g. the outlet 4 of the warming chamber. In such a case, the fluid flow and/or volume measurement may be obtained with only one temperature sensor which will is preferably located near the outlet of the warming system.

Figure 4:
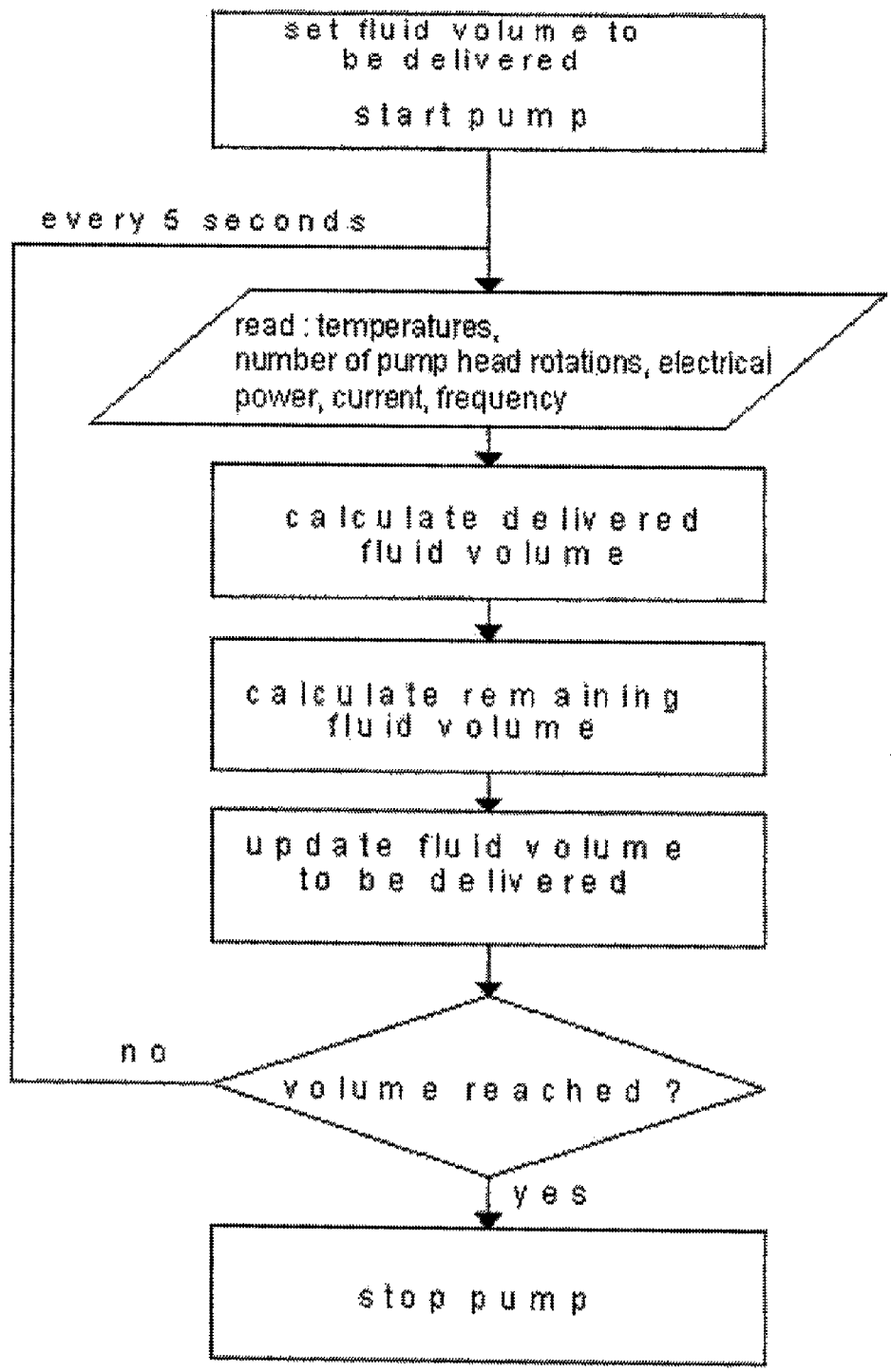

FIG. 4 represents a diagram of a method to compensate and correct the pumped fluid volumes from a pumping system in order to achieve the programmed fluid volumes which is administered and removed from the patient's body.

Pumped fluid volumes from peristaltic pumps or other type of pumps deliver the programmed fluid volume in accordance with their number of periodical movements, e.g. membrane movements. This fluid volume delivery is influenced by parameters which may increase or decrease the pumped or delivered fluid volume in comparison to the programmed fluid volume. A mass flow information in relation to the active pumping is advantageously used to correct or compensate the inadequate delivered fluid volume by adding or reducing number of turns in case of a peristaltic pump or number of activations in case of membrane pumps or others.

All influencing parameters such as fluid pressure before and after these pumps, fluid temperatures, pump designs, pump materials and dimensional part changes or pumping system aging can be corrected and therefore be used to balance the administered and removed fluids from the patient's body.

Figure 5:
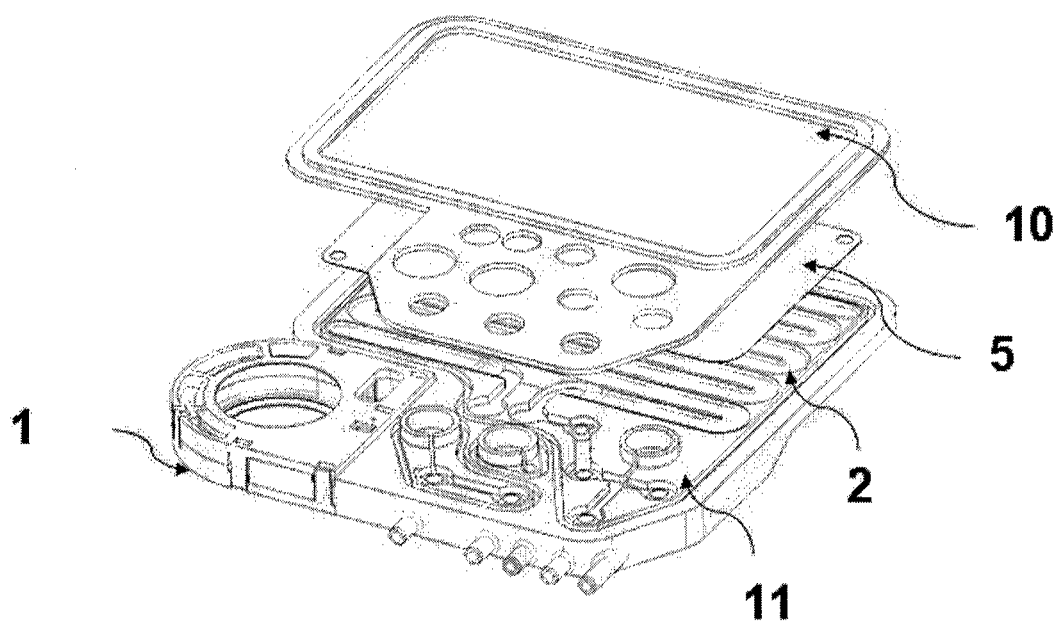

Finally, FIG. 5 shows a medical device with an integrated warming unit 2,5,10, a fluid distribution unit 11 and pumping unit 1 combined as a single disposable unit. Furthermore, the single disposable unit may also integrate an elastic membrane, which e.g. can be made from silicone (not illustrated).

In a preferred embodiment, the pumping unit and the warming unit are parts of the same single use unit which can also contain other elements such as dispatching valves. An example of such dispatching valves and pumping system is disclosed in international patent application WO 2005/009511 A2.

Of course the invention is not limited to the above cited examples.

The invention claimed is:

1. Medical device for the delivery and/or the extraction of fluid to and/or from a patient, said medical device comprising:
   a pumping unit for pumping a fluid,
   a warming chamber with an inlet and an outlet and containing a heating element for warming said fluid,
   fluid volume measuring means, and
   a fluid line crossing said pumping and warming units,
   wherein said heating element is adapted to be fully immersed in the fluid which is crossing said warming chamber and by the fact that said fluid volume measuring means comprise temperature sensing means adapted to measure the fluid temperature on at least two separate points, said fluid volume measuring means further comprising electrical parameter measuring means for determining at least one electrical parameter such as current, power, or frequency applied to said heating element.

2. Medical device according to claim 1 wherein said temperature sensing means consist of one single temperature sensor.

3. Medical device according to claim 2 wherein said single sensor is movably mounted in such a way as to measure the temperature on said two separate points.

4. Medical device according to claim 3 wherein said single sensor is rotatable.

5. Medical device according to claim 1 wherein said temperature sensing means comprise one fixed temperature sensor and one rotatable mirror which is adapted to reflect to said sensor the electromagnetic emission from said two separate points.

6. Medical device according to claim 5 wherein said sensor is an infrared sensor.

7. Medical device according to claim 1 wherein said sensor is located between said inlet and said outlet.

8. Medical device according to claim 1 wherein said temperature sensing means comprise two separate temperature sensors.

9. Medical device according to claim 8 wherein one sensor is close to said inlet while the other sensor is close to said outlet.

10. Medical device according to claim 1 furthermore comprising a processing unit connected to said temperature sensor(s), said processing unit being adapted to measure the volume flow through the warming unit, said volume flow being derived from said fluid volume measuring means.

11. Medical device according to claim 1 wherein said temperature sensor(s) is/are designed to permanently measure the temperature.

12. Medical device according to claim 1 wherein said temperature sensor(s) is/are designed to measure the temperature only during a predefined period during the warming phase.

13. Medical device according to claim 10 furthermore comprising fluid volume compensating means which are connected to said processing unit and to said pumping unit.

14. Medical device according to claim 1 wherein said heating element is made of metal and is designed to be heated by electromagnetic induction.

15. Medical device according to claim 14 wherein said heating element is a plate.

16. Medical device according to claim 14 wherein said heating element is a tube.

17. Medical device according to claim 1 wherein the length of said fluid line in the warming unit is maximized by means of fluid channels.

18. Medical device according to claim 1 furthermore comprising an inductive element consisting of at least one coil.

19. Medical device according to claim 18 wherein said coil is made of isolated strands having a diameter which is less than the penetration depth of the magnetic field in the heat conductive metallic element.

20. Medical device according to claim 19 wherein said diameter is at least two times less than said penetration depth.

21. Medical device according to claim 1 wherein said heating element functions as an electromagnetic shielding element to prevent electromagnetic perturbations outside of the warming chamber.

22. Medical device according to claim 1 wherein said heating element is made of a ferromagnetic material with a Curie temperature selected to limit overheating of the heat conductive metallic element.

23. Use of a medical device as defined in claim 1 for measuring the volume of the fluid crossing the device, said fluid volume being derived from the measurement of the temperature taken on at least two separate points of the fluid line and from the measurement of at least one electrical parameter such as current, power or frequency applied to said heating element.

24. Use according to claim 23 for compensating volume changes between a patient inflow and outflow.

25. Use according to claim 23 wherein a part of volume pumped is warmed for the sole purpose of measuring its flow characteristics.

* * * * *